US00PP36758P2

(12) United States Plant Patent
Lee

(10) Patent No.: US PP36,758 P2
(45) Date of Patent: Jun. 24, 2025

(54) ***RHODODENDRON* PLANT NAMED 'ROBLEZN'**

(50) Latin Name: ***Rhododendron* hybrid**
Varietal Denomination: ROBLEZN

(71) Applicant: Robert Edward Lee, Independence, LA (US)

(72) Inventor: Robert Edward Lee, Independence, LA (US)

(73) Assignee: PDSI, Loxley, AL (US)

( * ) Notice: Subject to any disclaimer, the term of this patent is extended or adjusted under 35 U.S.C. 154(b) by 0 days.

(21) Appl. No.: 18/935,725

(22) Filed: Nov. 4, 2024

(51) Int. Cl.
*A01H 5/00* (2018.01)
*A01H 6/36* (2018.01)

(52) U.S. Cl.
USPC ..... Plt./238

(58) Field of Classification Search
USPC ..... Plt./226, 238
See application file for complete search history.

(56) References Cited

U.S. PATENT DOCUMENTS

PP25,769 P2 * 8/2015 Pounders ..... A01H 6/364 Plt./240

* cited by examiner

*Primary Examiner* — Karen M Redden

(57) ABSTRACT

A new and distinct cultivar of *Rhododendron* plant named 'Roblezn' is disclosed, characterized by unique red-purple flowers colored Red-Purple 71A with an overall flush of N74B. Central petal section is irregularly dotted Greyed-Purple N186D. Plants bloom intermittently from early Spring until Fall. Plants have a strong root system, superior landscape qualities and are tolerant of pests. The new cultivar is a *Rhododendron*, suitable for ornamental garden purposes.

1 Drawing Sheet

Latin name of the genus and species: *Rhododendron* hybrid.

Variety denomination: 'ROBLEZN'.

BACKGROUND OF THE INVENTION

The new cultivar is a product of a planned breeding program by the inventor to develop new *Rhododendron* varieties with dark flower color, repeat blooming, all-around sturdiness, pest resistance and variable environmental adaptability. The seed and pollen parents were among unnamed, unpatented proprietary Azalea seedlings selected for the previously mentioned desired traits. The open field hand-pollination resulting in the new cultivar was made during 2012 at a nursery in Independence, Louisiana.

*Rhododendron* 'ROBLEZN' was found and selected in 2016 at the same nursery in Independence, Louisiana. The first asexual propagation occurred in the Fall of 2016 by semi-hardwood cuttings at the same nursery. 'ROBLEZN' has been found to retain its distinctive characteristics through successive asexual propagations over multiple generations.

SUMMARY OF THE INVENTION

The cultivar 'ROBLEZN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ROBLEZN'. These characteristics in combination distinguish 'ROBLEZN' as a new and distinct *Rhododendron* cultivar:

1. Single, self-cleaning flowers with unique red-purple coloring.
2. Repeat blooming in spring, summer and fall.
3. Superior landscape qualities; tolerant to environmental and climatic conditions.
4. Tolerant to pests.
5. Strong root system.

COMPARISON TO PARENT VARIETIES

Parent comparisons are unavailable as exact parentage cannot be determined.

COMMERCIAL COMPARISON

'ROBLEZGN' can be compared to the commercial variety *Rhododendron* 'ROBLEZG', currently pending with application Ser. No. 18/935,721. Plants of the new cultivar 'ROBLEZN' are similar to plants of 'ROBLEZG' in most horticultural characteristics. Plants of the new cultivar 'ROBLEZN', however, differ in the following:

1. Mature upper petal color of 'ROBLEZN' is Red-Purple 71A with an overall flush of N74B. Central petal section is irregularly dotted Greyed-Purple N186D. Mature upper petal color of 'ROBLEZG' is Red-Purple 61C with a slight sheen of N57C and a distal petal blotch composed of linear dots colored Red 60A.
2. Young branches of 'ROBLEZN' are colored 'Greyed-Orange 165B; young branches of 'ROBLEZG' are colored Yellow-Green 144B.

3. Flowers of 'ROBLEZN' are 5 cm long and 8.5 cm in (on average); flowers of 'ROBLEZG' are diameter are 3.8 cm long and 6.8 cm in diameter (on average).

BRIEF DESCRIPTION OF THE PHOTOGRAPH

'ROBLEZN' is illustrated by the accompanying photograph, which shows the flowering plant of 'ROBLEZN' in a two-gallon container at approximately 2-years old. The colors shown are as true as can be reasonably obtained by conventional photographic procedures. Colors in the photograph may differ slightly from the color values cited in the detailed botanical description, which accurately describes the new hybrid *Rhododendron.*

DETAILED BOTANICAL DESCRIPTION

The following is a detailed description of the botanical characteristics of the new and distinct *Rhododendron* 'ROBLEZN'. The detailed description was taken of a 2-year-old 2-gallon plant grown in Loxley, AL during 2024. All colors cited herein refer to The Royal Horticultural Society Colour Chart (The Royal Horticultural Society (R.H.S.), London, 2015 Edition. Where specific dimensions, sizes, colors, and other characteristics are given, it is to be understood that such characteristics are approximations or averages set forth as accurately as is practicable.

Botanical classification: *Rhododendron* hybrid 'ROBLEZN'.

ROOTS

Root description: Fine, fibrous young roots, well branched. Colored near RHS Grey-Brown 199A.

PLANT

Plant type: Flowering shrub.
Growth habit: Upright.
Height: Approximately 40 cm to top of foliar and flowering plane.
Width: Approximately 38 cm.
Growth rate: Moderate.
Vigor: Moderate.
Branching characteristics: Moderately well-branched, average 4 to 8 primary branches from the center of the plant. Branches occur at approximately 25° to 60° angles.
Length of primary branches: Average range 16 to 28 cm.
Diameter of primary branches: Average range 6 mm to 10 mm.
Primary branch strength: Very strong, difficult to break.
Primary branch color:
- *Young branches.*—Near RHS Greyed-Orange 165B.
- *Woody branches.*—Near RHS Yellow-Green 146C streaked Grey-Green 197B.

Primary branch texture:
- *Immature growth.*—Hirsute.
- *Older growth.*—Slightly scaly.

Lateral branches:
Number of lateral branches: Approximately 3 to 5 per primary branch.
Length of lateral branches: Average 8 cm to 12 cm.
Diameter of lateral branches: Average 4 to 5 mm.
Lateral branch strength: Very strong, flexible.
Lateral branch color: RHS Yellow-Green 144C, lightly flushed Greyed-Red 181D.
Lateral branch texture: Pubescent, hairs appressed.
Internode length: Average range 2.5 to 3.5 cm.

FOLIAGE

Leaf:
- *Type.*—Simple.
- *Arrangement.*—Alternate.
- *Length.*—Approximately 3.2 cm, excluding petiole.
- *Width.*—Approximately 2 cm.
- *Shape.*—Obovate.
- *Apex.*—Mucronate.
- *Base.*—Attenuate.
- *Attachment.*—Stalked.
- *Margin.*—Entire.
- *Texture of top surface.*—Rough.
- *Texture of bottom surface.*—Rough.
- *Appearance of top surface.*—Glossy.
- *Appearance of bottom surface.*—Matte.
- *Color.*—Young foliage upper side: Near RHS Yellow-Green 143A. Young foliage under side: Near RHS Yellow-Green 143C. Mature foliage upper side: Near RHS Green 139A. Mature foliage under side: Near RHS Green 137C.
- *Venation.*—Type: Pinnate. Venation color upper side: Near RHS Yellow-Green 144B. Venation color under side: Near RHS Yellow-Green 144B.
- *Petiole.*—Length: About 2 to 4 mm. Diameter: About 2 mm. Color: Upper Surface: Near RHS Yellow-Green 144B. Lower Surface: Near RHS Yellow-Green 144B. Texture of top surface: Rough. Texture of bottom surface: Rough.

FLOWER

Natural flowering season: Intermittently from early Spring through Fall.
Arrangement: Axillary clusters of single open funnel shaped individual flowers. Typically 5 flowers per cluster.
Inflorescence:
- *Height.*—Average 8 cm.
- *Diameter.*—Average range 12 to 18 cm.

Peduncle:
- *Length.*—Average 1 cm.
- *Diameter.*—4 mm.
- *Color.*—Near RHS Greyed-Red 178C.
- *Texture.*—Hirsute.
- *Aspect.*—Straight. Angle of attachment, approximately 15° angle from stem.

Pedicel:
- *Length.*—Average 20 mm.
- *Diameter.*—3 mm.
- *Color.*—Near RHS Yellow-Green 144C. Occasionally flushed Red-Purple 67A.
- *Texture.*—Densely pubescent.
- *Aspect.*—Straight. Approximately 25° angle from stem.

Flowers:
- *Length.*—Average 5 cm.
- *Diameter.*—Average 8.5 cm.
- *Aspect.*—Outward and upward facing.
- *Persistence.*—Self-cleaning.
- *Fragrance.*—None detected.

Tube:
- *Length.*—Average 20 mm.
- *Width a widest point.*—Approximately 1 cm.
- *Width and narrowest point.*—Approximately 8 mm.

Petals:

*Quantity.*—5.

*Unfused petal segments.*—Length: Approximately 3 to 3.9 cm. Width: Approximately 3 cm.

*Apex.*—Blunt, rounded with shallow (0.05 mm), irregular lobes or notches.

*Shape.*—Unfused portion, obovate.

*Margin.*—Entire. Moderately ruffled.

*Arrangement.*—Slightly to moderately overlapping, bilateral symmetry dissecting bottom petal. Petals fused approximately ⅓ fused from base.

*Texture.*—Smooth, all surfaces.

*Color.*—Upper surface at first opening: RHS Red-Purple 70B with an overall lush of N74B. Central section irregularly dotted Greyed-Purple N186B. Under surface at first opening: RHS Red-Purple 70B with an overall flush of N74B. Central section faintly and irregularly dotted Greyed- Purple N186B. Streak/flush near mid-vein near Red-Purple 58B. Inner surface at maturity: RHS Red-Purple 70A with an overall flush of N74B. Central section (throat) irregularly dotted Greyed-Purple N186D. Outer surface at maturity: RHS Red-Purple 70A with an overall flush of N74B. Central section faintly and irregularly dotted Greyed-Purple N186B. Fading: Significant change not observed compared to mature color.

Bud:

*Shape.*—Elliptic.

*Length.*—4.8 cm.

*Diameter.*—1.6 cm.

*Color.*—Near RHS Red-Purple 70A.

Sepals:

*Quantity per flower.*—5.

*Shape.*—Narrow deltate.

*Length.*—7 mm.

*Width.*—3 mm.

*Apex.*—Acute.

*Base.*—Fused.

*Margin.*—Entire.

*Texture.*—Highly pubescent.

*Color.*—Inner Surface: Near RHS Yellow-Green 143B. Outer Surface: Near RHS Yellow-Green 143C.

REPRODUCTIVE ORGANS

Stamens:

*Number.*—8.

*Length.*—3.7 cm.

*Filament color.*—RHS Red-Purple 68A, upper ⅕ N74B.

*Protrusion.*—Slightly protruding, greater protrusion with age.

*Anthers.*—Length: Approximately 3 mm. Color: Near RHS Greyed-Purple 187B. Pollen: Not observed.

Pistil:

*Number.*—1.

*Length.*—5.8 cm.

*Style.*—Length: Average 5.5 cm. Color: Near RHS Red-Purple N57A.

*Stigma.*—Shape: Globular. Color: Near RHS Greyed-Purple 187B.

*Ovary.*—Length: 3 mm. Diameter: Approximately 3 mm. Texture: Sericeous. Color: Near RHS Yellow-Green 144C.

OTHER CHARACTERISTICS

Fruit and seed: Not observed.

Disease and pest resistance: Field observations show tolerance to typical pests of *Rhododendron*, which include lace wings and red mites. The new cultivar did not show susceptibility to root diseases observed in other cultivars in the same field test.

Temperature tolerance: USDA Zones 6-10.

What is claimed is:

1. A new and distinct cultivar of *Rhododendron* plant named 'Roblezn' as herein illustrated and described.

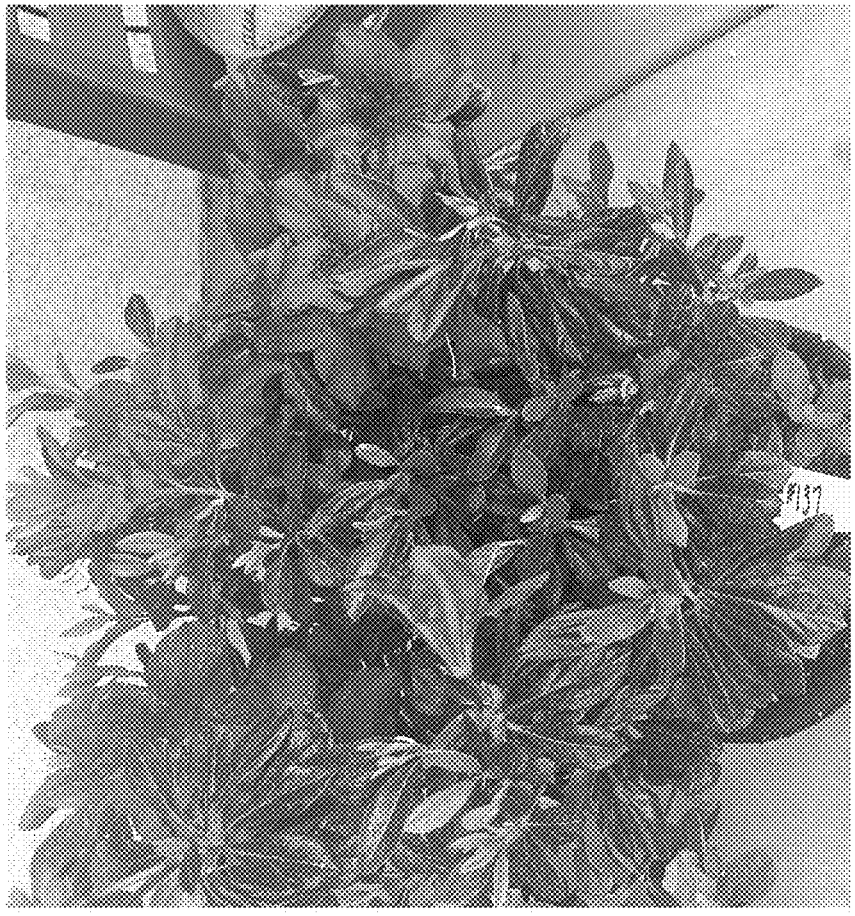

* * * * *